United States Patent [19]

Linden

[11] Patent Number: 4,832,601
[45] Date of Patent: May 23, 1989

[54] ADJUSTABLE SUPPORT FOR A PROSTHETIC TOOTH AND METHOD

[75] Inventor: Harry A. Linden, Santa Barbara, Calif.

[73] Assignee: Hall Surgical, Carpinteria, Calif.

[21] Appl. No.: 128,751

[22] Filed: Dec. 4, 1987

[51] Int. Cl.$^4$ .............................................. A61C 8/00
[52] U.S. Cl. ........................................................ 433/173
[58] Field of Search ................ 433/173, 174, 175, 176

[56] References Cited

U.S. PATENT DOCUMENTS 3,732,621  5/1973  Bostrom ............................. 433/174

Primary Examiner—Robert Peshock
Attorney, Agent, or Firm—Stuart E. Krieger

[57] ABSTRACT

The adjustable support for a prosthetic tooth includes an abutment member having an opening for reception of a bolt member that engages with a nut member. The abutment member is sandwiched between a head portion of the bolt member and an enlarged collar portion of the nut member. The engaging surfaces between the head portion and the abutment member and between the abutment member and the enlarged collar portion of the nut member are of complementary shape with respect to each other to permit pivotal adjustment of the abutment member with respect to the bolt and nut members. The abutment member is thus pivoted to a desired position and the bolt and nut members are tightened to lock the abutment member in the desired position. A prosthetic tooth having an opening of complementary shape with respect to the abutment member engages the abutment member to assume the angular orientation of the abutment member. The adjustable support and prosthetic tooth are affixed in a foundation implant that is locked into the jawbone. The prosthetic tooth and the adjustable support are thus rigidly secured to the jawbone.

16 Claims, 3 Drawing Sheets

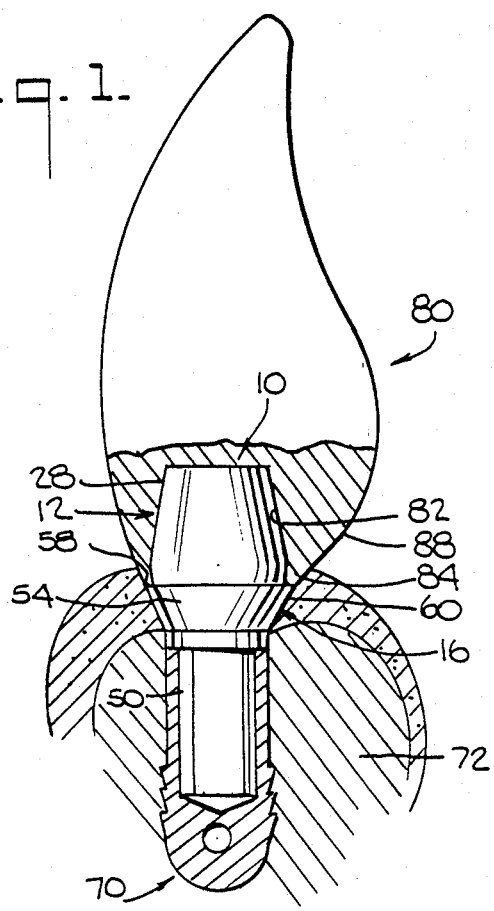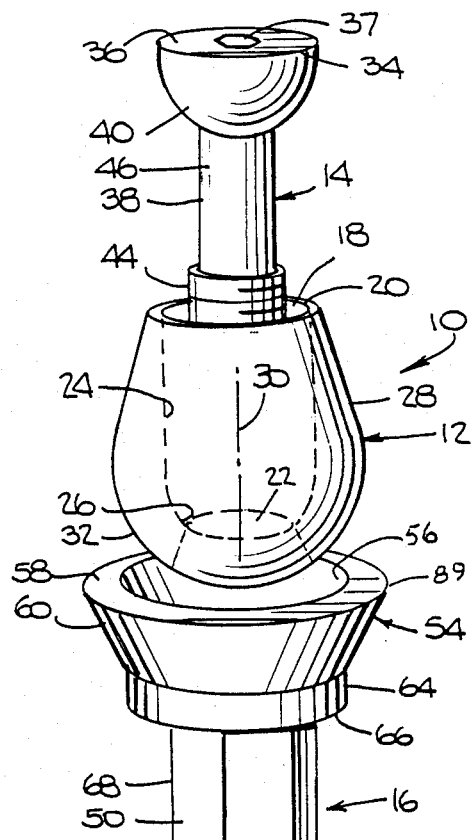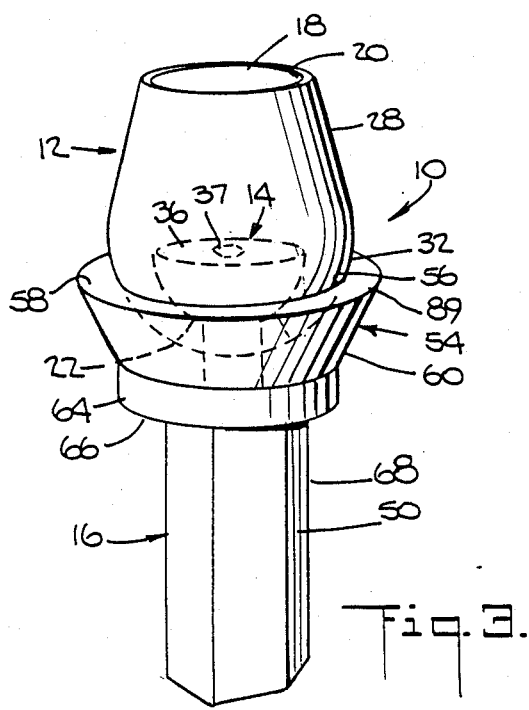

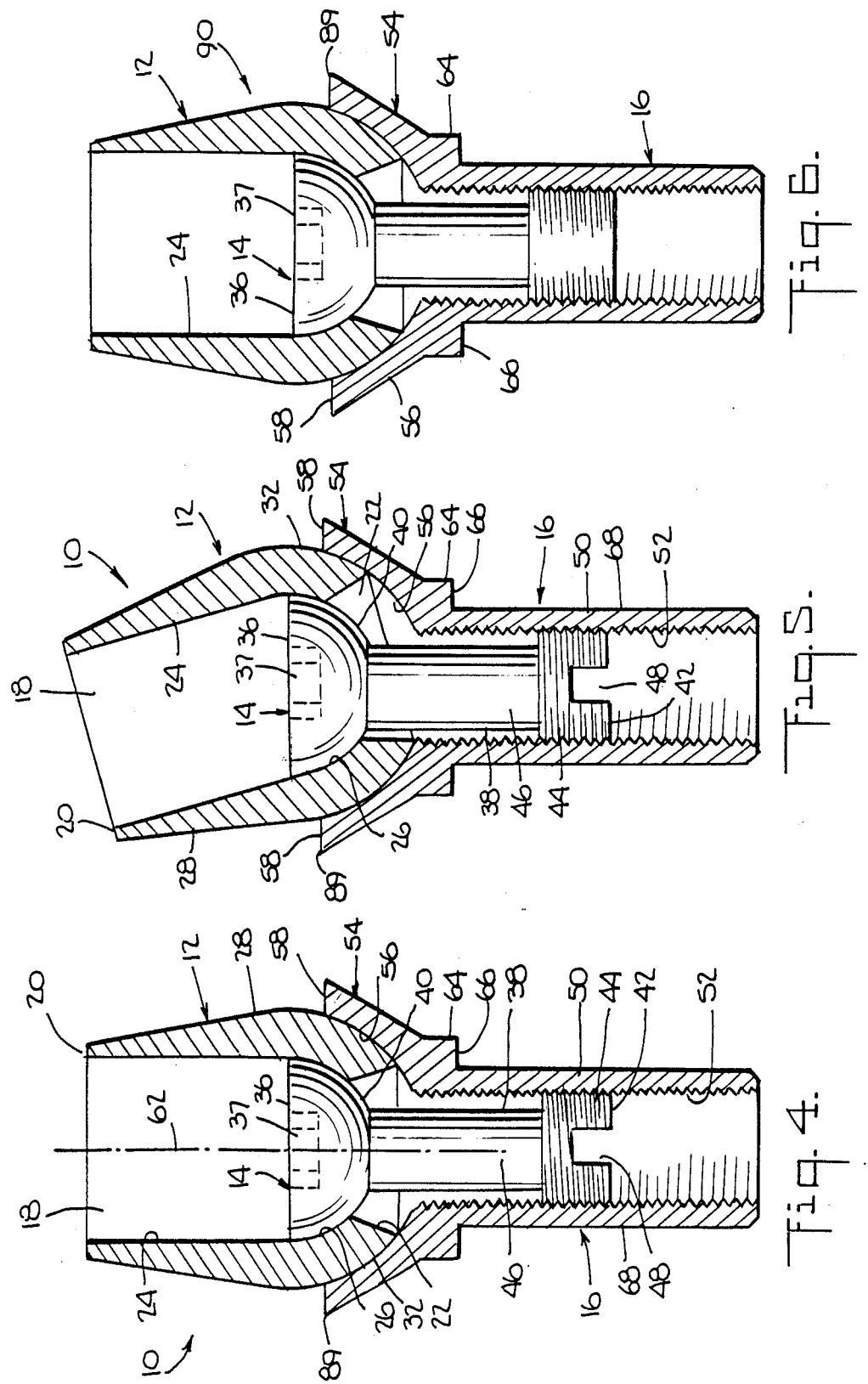

4,832,601

ADJUSTABLE SUPPORT FOR A PROSTHETIC TOOTH AND METHOD

BACKGROUND OF THE INVENTION

This invention relates to dental prostheses and more particularly to an adjustable support for orienting and holding a prosthetic tooth or appliance at a preselected angle.

The installation of a prosthetic tooth usually requires a foundation implant in the jawbone for receiving a support arrangement for holding the prosthetic tooth. Known support arrangements for prosthetic teeth are usually inserted directly into a foundation implant such as shown in U.S. Pat. No. 4,657,510. The axis of the prosthetic tooth closely aligns with substantially aligned axes of the foundation implant and the tooth support.

Thus the orientation of the prosthetic tooth usually follows the orientation of the foundation implant. If slight changes are needed in the angular position of the prosthetic tooth relative to the foundation implant it is often necessary to machine the tooth or the tooth support to the desired angle, or bend the tooth support to the desired angle. Machining of the tooth support is a costly and time consuming procedure and the bending of a tooth support can cause stress cracking and reduce the strength of such support.

A recent development in response to these problems is a device sold under the trademark Robutment by Ventplant Corporation of Philadelphia, Pa. The Robutment device includes two arms pivoted at a ball joint for adjustment purposes. One arm locks into the jawbone and the other support arm is inserted in a hole in the prosthetic tooth. Since the support arm is generally cylindrical, a drilled hole of precise dimension must be made in the prosthetic tooth to properly accommodate the cylindrical support arm. In order to lock the Robutment device in an adjusted position the exterior surface of an abutment portion must be held rigidly with a holding tool. Tool marks and scratches can thus occur on surfaces that make intimate contact with the mucosa thereby causing irritation. Another disadvantage of the Robutment device is that the prosthetic tooth must be feathered to tapered edge against the surface of the cylindrical support arm, thus requiring precise machining after the tooth is in place.

It is thus desirable to provide an adjustable support for a prosthetic tooth that can be rigidly secured to an implant in a selected position without the need for drilled holes of precise dimension in the prosthetic tooth and without the need for feathering the prosthetic tooth to a tapered edge. It is further desirable to provide an adjustable support for a prosthetic tooth that can be tightened in a desired position without scratching surface portions of the support that contact the mucosa.

OBJECTS AND SUMMARY OF THE INVENTION

Among the several objects of the invention may be noted the provision of a novel adjustable support for a prosthetic appliance, a novel adjustable support for a prosthetic tooth, a novel adjustable support for a prosthetic tooth which can be rigidly locked in position at a preselected angle with respect to a foundation implant, a novel adjustable support for a prosthetic tooth that has a ledge on which the tooth bottoms to facilitate the finishing of the tooth surface, a novel adjustable support for a prosthetic tooth which includes a ledge having an edge that the prosthetic tooth ma be tapered to for finishing purposes, a novel adjustable support for a prosthetic tooth with an abutment portion that is tapered to engage a tapered bore in the prosthetic tooth, a novel adjustable support for a prosthetic tooth that can be preset to a desired angle after an initial fitting in a foundation implant and a novel method of angularly adjusting a support for a prosthetic tooth.

Other objects and features of the invention will be in part apparent and in part pointed out hereinafter.

The adjustable support arrangement for an artificial tooth, in accordance with one embodiment of the invention, includes an abutment member having an exterior surface portion that is tapered and an opening defining an interior surface in the abutment member. The opening defines a mouth portion at one end of the abutment member and an exit portion and an opposite end. The exterior surface of the abutment is rounded at the exit portion.

A bolt member receivable in the abutment member opening has a convex head portion that contacts a concave interior surface of the abutment at the exit portion to permit adjustment of the abutment member to different predetermined pivotal positions with respect to the bolt head. The bolt member also includes a stem portion that extends from the exit portion of the abutment member.

A nut member engages the stem portion of the bolt member and includes an enlarged section with a concave engagement portion that engages a convex surface portion of the abutment member at the exit portion. The engagement between the convex exterior surface of the abutment member and the concave engagement portion of the nut member also permits adjustment of the abutment member to different predetermined pivotal positions. The abutment member can be rigidly locked into a selected pivotal position when the nut member and the bolt member are engaged a predetermined amount.

The bolt member is formed with at least one recess at the head end or the stem end for engagement with a driving member. The nut member is elongated such that the stem portion is recessed in the nut member when the nut member and the bolt member are engaged the predetermined amount.

In using the adjustable support for a prosthetic tooth the bolt member is inserted in the opening in the abutment member such that the head portion of the bolt member engages the interior surface of the abutment member at the exit portion. The nut member is threaded onto the stem portion of the bolt member until the concave engagement portion engages the convex surface portion of the abutment member. Thus the abutment member is sandwiched between the head portion of the bolt member and the concave engagement portion of the nut member.

Complementary surface engagements between the head portion of the bolt member and the interior surface of the abutment member, and between the exterior surface of the abutment member and the nut member permit positioning of the abutment member at a preselected angle with respect to aligned axes of the nut member and the bolt member.

A prosthetic tooth having a tapered recess is slipped onto the abutment member, and the tooth and support assembly are temporarily installed in a foundation implant previously embedded in the jawbone. The disposition of the support into the foundation implant permits adjustment of the prosthetic tooth to a desired angle. Adjustment is made possible by a slight tightening of the bolt and nut members prior to inserting the support in the foundation implant. Slight tightening of bolt and nut members provides a slight detent of the abutment member which is easily overcome by movement of the prosthetic tooth for adjustment purposes to establish a desired angle for the abutment member.

The prosthetic tooth and support assembly are then removed from the foundation implant. The prosthetic tooth is removed from the abutment member, which is detented at the desired angle. The bolt and nut are further tightened to rigidly secure the abutment member at the desired angle. The support is reinstalled in the foundation implant and the prosthetic tooth is cemented on the abutment member. If desired, the prosthetic tooth can be cemented to the abutment member before the support is reinstalled in the foundation implant. The angling of the abutment and cementing to the tooth can also be accomplished at a crown and bridge lab that fabricates the appliance.

The nut member has a hexagonal peripheral portion that does not contact the mucosa. Tightening of the nut member to the bolt member is easily accomplished by appropriate tools to engage the hexagonal periphery and to drive the bolt member via the driving recesses formed therein.

The sidewalls of the tooth are finished to form a smooth continuation with the enlarged section of the nut member. This finishing operation is facilitated by provision of a ledge portion on which the tooth bottoms. Thus the tooth is finished to an edge of the ledge portion and need not be tapered to form a feathered edge.

The interior surface of the abutment member can also be provided with threads to accommodate support structure for a bridge. Under this arrangement, more than one support can function together to provide support for the bridge.

The invention accordingly comprises the constructions and the method hereinafter described, the scope of the invention being indicated in the claims.

DESCRIPTION OF THE DRAWINGS

In the accompanying drawings,

FIG. 1 is an elevational view, partly shown in section, of the adjustable support for a prosthetic tooth incorporating one embodiment of the invention;

FIG. 2 is an exploded perspective view thereof;

FIG. 3 is a perspective view showing the support in assembled condition;

FIG. 4 is an enlarged sectional view thereof;

FIG. 5 is a view similar to FIG. 4 showing the support positioned at a preselected angle;

FIG. 6 is a sectional view showing another embodiment of the invention;

Corresponding reference characters indicate corresponding parts throughout the several views of the drawings.

DETAILED DESCRIPTION OF THE INVENTION

Figure 7:
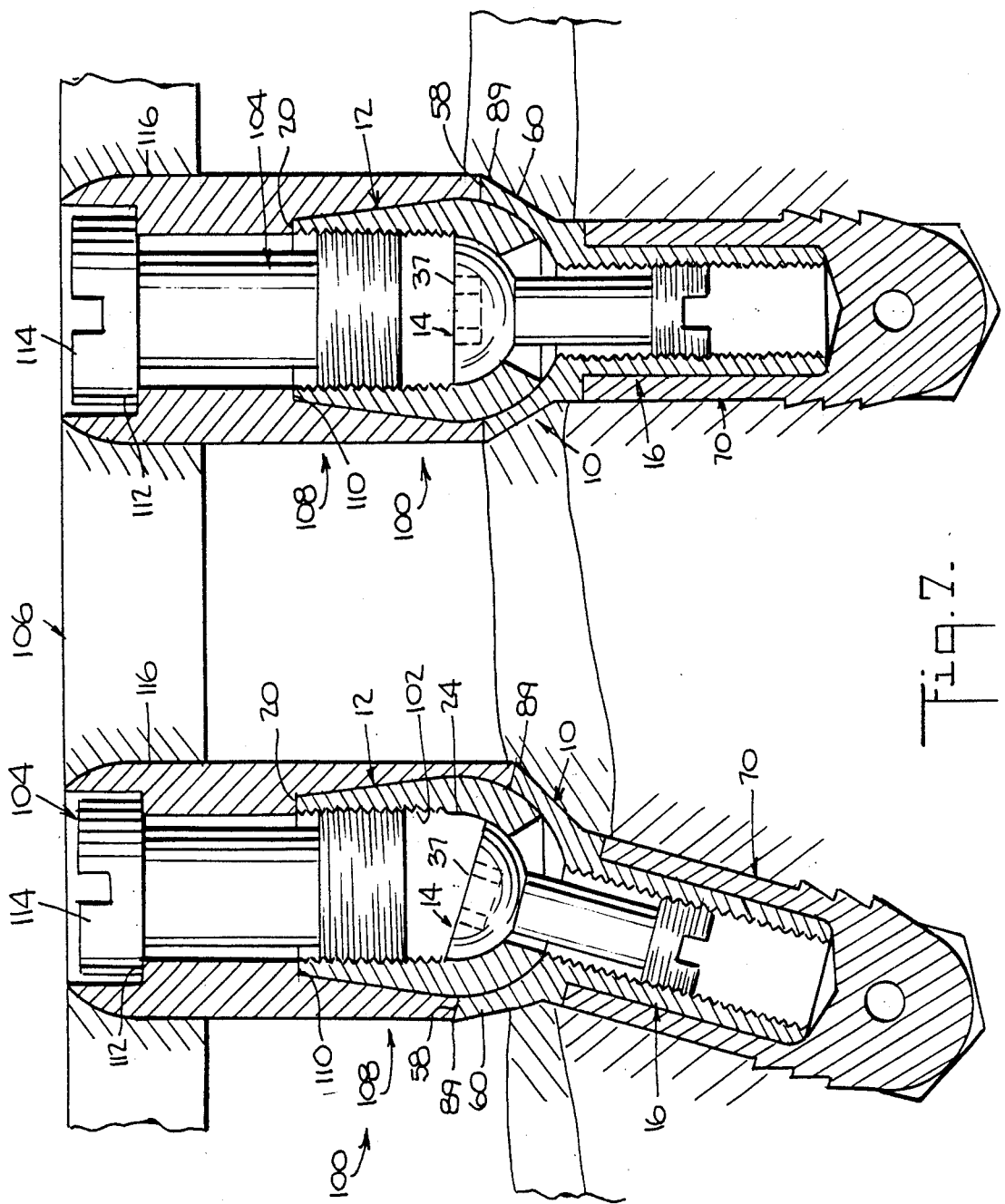
FIG. 7 is a sectional view showing a further embodiment of the invention.

An adjustable support for a prosthetic tooth incorporating one embodiment of the invention is generally indicated by the reference number 10 in FIGS. 1–6.

The support 10 includes an abutment member 12 that accomodates a bolt member 14 (FIG. 2) which engages a nut member 16.

The abutment member 12 which can be formed of titanium, is bulbous in shape. The abutment member 12 includes an opening 18 having a mouth portion 20 at one end and an exit portion 22 at the opposite end. The opening 18 thus defines a generally cylindrical interior surface 24 (FIGS. 4–6) from the mouth portion 20 toward the exit portion 22 terminating in a generally concave form 26 at the exit portion 22. The abutment member 12 further includes an exterior surface 28 that tapers away from an axis 30 (FIG. 2) of the opening 18. The exterior surface 28 is of convex form 32 at the exit portion 22.

The bolt member 14, which can be formed of stainless steel, includes a head portion 34 having a flat end 36. A hexagonal socket 37 is formed in the flat end 36. The head portion 34 is of rounded convex form from the flat end 36 toward a stem portion 38, the rounded convex form being indicated at 40. The rounded surface 40 is of complementary shape with respect to the concave portion 26 of the abutment member 12. The head portion 34 is thus receivable in the mouth portion 20 of the opening 18 but cannot pass through the exit portion 22 of the opening 18. The abutment member 12 can thus be pivoted with respect to the head portion 34.

Referring to FIGS. 4 and 5, the stem portion 38 of the bolt member 14 has a free end portion 42 with threads 44 formed thereon. A reduced unthreaded portion 46 of the stem 38 extends from the threads 44 to the rounded surface 40 of the head 34. If desired, a slot 48 is formed in the free end 42 the stem 38.

The nut member 16, which can be formed of titanium, includes an elongated sleeve portion 50 formed with internal threads 52. An enlarged collar portion 54 is formed at an end of the sleeve 50. The enlarged collar portion 54 includes an inner concave surface 56 that diverges away from the internal threads 52. The inner concave surface 56 is of complementary shape with respect to the convex form 32 of the abutment member 12. The abutment member 12 can thus be pivoted with respect to the concave surface 56.

An annular ledge surface 58 is formed at a free end of the enlarged collar portion 54. An exterior surface 60 of the enlarged collar portion 54 tapers toward an elongated axis 62 FIG. 4. of the sleeve 50 which aligns with the axis of the bolt member 14. The enlarged collar portion 54 also includes a rim portion 64 having a landing surface 66. The rim portion 64 can be of any selected height along the axis 30. A hexagonal exterior surface 68 is formed on the sleeve 50 up to the landing surface 66.

In using the support 10, a foundation implant 70 is first embedded in a jawbone 72 below the gum 74, as shown in FIG. 2. The implant 70 is rigidly locked in position in the jawbone 72 by means of shingle shaped projecting members 76 that form undercuts in the jawbone 72. The implant 70 includes a hexagonal recess 76 formed in an end surface 78. The hexagonal recess 76 is of complementary size with respect to the hexagonal surface 68 of the nut member 16. Further details of the structure and operation of the foundation implant 70 are contained in my copending application.

The bolt member 14 is disposed in the opening 18 of the abutment member 12 such that the rounded convex form 40 of the head portion 34 engages the concave surface 26 of the opening 18. The stem portion 38 thus projects from the exit portion 22 of the opening 18. The nut member 16 is threaded to the threaded portion 44 of the stem 38 until the inner concave surface 56 engages the convex portion 32 of the abutment member 12. Relative tightening between the bolt member 14 and the nut member 16 is accomplished by holding the hexagonal surface 68 of the nut member 16 with a suitable holding tool (not shown) and using a suitable driving tool such as an Allen or Bondus wrench (not shown) to engage the hexagonal hole 37 of the nut member 14.

The bolt member 14 and the nut member 16 are tightened a predetermined amount to slightly detent the abutment member 12 between the rounded surface 40 of the bolt member 14 and the inner concave surface 56 of the nut member 16. Thus the abutment member 12 at this stage is not rigidly locked in position.

Referring to FIG. 1, the support 10, as assembled, is fitted with a prosthetic tooth 80 having a tapered opening 82 that accomodates the exterior surface 28 of the abutment member 12. The prosthetic tooth 80 has a base surface 84 that bottoms against the ledge surface 58 of the enlarged collar portion 54.

The prosthetic tooth 80 at this stage of the installation is not tightly affixed to the abutment member 12.

The support 10 and the prosthetic tooth 80 are located for positioning of the tooth 80 by inserting the hexagonal sleeve 50 of the nu member 16 into the hexagonal recess 76 of the foundation implant 70 or laboratory analog. A desired orientation angle for the prosthetic tooth 80 is determined relative to other teeth (not shown). The abutment member 12, with the prosthetic tooth 80, is adjusted to the desired angle by overcoming the slight detent between the abutment member 12 and the bolt member 14 and nut member 16. The support 10 and the prosthetic tooth 80 are then removed from the foundation implant 70 or analog. The prosthetic tooth 80 is removed from the abutment member 12, and the bolt member 14 and nut member 16 are further tightened to rigidly lock the abutment member 12 in the desired position.

The prosthetic tooth 80 is again installed on the abutment member 12, either before or after the support 10 is repositioned in the foundation implant 70. The support 10 is rigidly secured to the foundation implant 70 in any suitable known manner, as by cementing or mechanical affixation. The base surface 84 of the prosthetic tooth 80 is ground slightly to enable the tapered opening 82 in the tooth 80 to tightly engage the abutment member 12, and to permit the base surface 84 to engage the ledge surface 58.

Any sidewall portions 88 of the prosthetic tooth 80 that overhang the ledge surface 58 can be finished to the edge 89 of the ledge 58. The finished sidewall 88 of the tooth 80 thus form a continuation with the exterior surface 60 of the enlarged collar portion 54. Since the sidewall 88 of the tooth 80 is finished to the edge 89 there is no need to taper the sidewall 88 to form an edge. Under this arrangedment there is a smooth, continuous surface transition from the tooth 80 to the support 10 without the need to feather the sidewall 88 of the tooth.

The prosthetic tooth 80 is bonded or otherwise affixed in a known manner to the abutment member 12 to form a permanent connection.

Another embodiment of the adjustable support for a prosthetic tooth is generally indicated by the reference number 90 in FIG. 6. The support 90 differs from the support 10 by virtue of the elimination of the slot 48 in the bolt member 14. The socket recess 37, which is engaged by a suitable drive member such as an Allen o Bondus wrench, permits tightening of the bolt member 14 and nut member 16, in certain instances, without removing the support 10 from the foundation implant 70 after prepositioning of the prosthetic tooth 80. The support 90 is otherwise similar in structure and operation to the support 10.

Another embodiment of the support is generally indicated by the reference number 100 in FIG. 7. The support 100 includes a support 10 provided with internal threads 102 formed on the cylindrical surface 24 of the abutment member 12. The support 100 is thus capable of receiving a threaded member 104 for securing a bridge member 106 in position, with cooperation of one or more additional support members 100. The bridge member 106, shown in simplified schematic form, is held in position by adapter members 108 that surround the threaded member 104, and the abutment member 12.

The adapter member 108 is formed of any suitable known precious metal coping . The precious metal coping that is a constituent of the adapter member 108 is finished to the edge 89 of the ledge 58 to provide a smooth continuation with the exterior surface 60. The adapted member 108 includes a circular step 110 that engages the mouth portion 20 of the abutment member 12 and an annular ledge 112 that engages a head 114 of the threaded member 104.

And end portion 116 of the adapter member 108 is welded or otherwise secured to the bridge member 106. The support 100 thus permits necessary adjustment of the supports 10 to properly position and hold the bridge 106 in the jawbone 72.

Some advantages of the present invention evident from the foregoing description include a support for a prosthetic tooth which is easily adjustable to a desired angular position. The support can be rigidly locked in the desired angular position before or after being permanently affixed to a foundation implant. A further advantage is that the prosthetic tooth need not be precision drilled or sized before engagement with the support. The ledge surface on the enlarged collar portion permits finishing of the tooth sidewalls without the need for feathering the tooth surface.

A still further advantage is that any tools used for tightening of the support do not mar, scratch or otherwise blemish the surface of the support which engages the mucosa. The support is easily adaptable to support a bridge and can function together with other similar supports for such purpose.

In view of the above, it will be seen that the several objects of the invention are achieved and other advantageous results attained.

As various changes can be made in the above constructions and methods without departing from the scope of the invention, it is intended that all matter contained in the above description or shown in the accompanying drawings shall be interpreted as illustrative and not in a limiting sense.

What is claimed is:

1. An adjustable support for a prosthetic tooth comprising,
  (a) a hollow prosthesis receiving abutment member having two open ends, an exterior surface and an interior surface in said abutment member,
  (b) a bolt member having a head portion receivable in said abutment member for engagement with said interior surface, said head portion being formed with a recess for engagement with a drive member, said head portion also being of a complementary shape with respect to said interior surface, said bolt member further including a stem portion extendable out of one of said open ends when said head portion is engaged with said interior surface, and
(c) a nut member engagable with the stem portion of said bolt member and the exterior surface of said abutment member such that said abutment member can be sandwiched between the head portion of said bolt member and said nut member when said nut member and said bolt member are engaged a predetermined amount.

2. An adjustable support for a prosthetic tooth comprising:
(a) a hollow prosthesis receiving abutment member having two open ends, an exterior surface and an interior surface in said abutment member,
(b) a bolt member having a head portion receivable in said abutment members opening for engagement with said interior surface, said head portion being of a complementary shape with respect to said interior surface, said bolt member further including a stem portion extendable out of said opening when said head portion is engaged with said interior surface, said stem portion being formed with recess for engagement with a drive member,
(c) a nut member engagable with the stem portion of said bolt member and the exterior surface of said abutment member such that said abutment member can be sandwiched between the head portion of said bolt member and said nut member when said nut member and said bolt member are engaged a predetermined amount.

3. The adjustable support as claimed in claim 1 or 2 wherein said interior surface includes a concave portion and said head portion includes a complementary shaped convex portion engagable with said concave portion.

4. The adjustable support as claimed in claim 1 or 2 wherein said nut member has a complementary surface portion with respect to the exterior surface of said abutment member.

5. The adjustable support as claimed in claim 4 wherein said head portion is of complementary shape with respect to said interior surface to permit surface-to-surface contact between said head portion and said abutment member, and surface-to-surface contact between said nut member and said abutment member when aid abutment member is in said sandwiched position.

6. The adjustable support as claimed in claim 4 wherein said exterior surface includes a convex portion and said nut member includes a complementary shaped concave portion engagable with said convex portion.

7. The adjustable support as claimed in claim 4 wherein said nut member has an enlarged section incorporating said complementary surface portion, and a sleeve-like section depending from said enlarged section, said sleeve-like section including internal threads for engagment with the stem portion of said bolt member.

8. The adjustable support as claimed in claim 4 wherein said nut member has an enlarged section incorporating said complementary surface portion, and said enlarged section includes a ledge portion projecting away from the exterior surface of said abutment member.

9. The adjustable support as claimed in claim 1 or 2 wherein said abutment member has one end and said opening has a mouth portion at said one end, and said abutment member has an opposite end and said opening has an exit portion at said opposite end.

10. The adjustable support as claimed in claim 9 wherein the interior surface of said abutment member is threaded from said mouth portion towards said exit portion.

11. An adjustable support for a prosthetic tooth comprising:
(a) a hollow prosthesis receiving abutment member having two open ends, an exterior surface and an interior surface in said abutment member, said abutment member having one end wherein said opening has a mouth portion and an opposite end wherein said opening has an exit portion, said exterior surface being rounded at said exit portion, said abutment member being tapered from said mouth portion toward said exit portion and rounded at said exit portion,
(b) a bolt member having a head receivable in said opening, said head having a first engagement portion engagable with said interior surface at said exit portion, to permit positioning of said abutment member at different predetermined pivotal positions with respect to said head, said bolt member having a stem portion extendable out of said exit portion when the first engagement portion of said head is engaged with said interior surface at said exit portion, and
(c) a nut member engagable with the stem portion of said bolt member and having an enlarged section with a second engagement portion engagable with the exterior surface at said exit portion to permit positioning of said abutment member at said different predetermined pivotal positions in engagement with said second engagement portion, to enable said abutment member to be rigidly locked between said nut member and said bolt member into one of said predetermined pivotal positions when said nut member and said stem portion are engaged a predetermined amount.

12. The adjustable support as claimed in claim 11 wherein the interior surface of said abutment member is threaded from said mouth portion toward said exit portion.

13. The adjustable support as claimed in claim 11 wherein said stem portion is recessed in said nut member when said nut member and said stem portion are engaged said predetermined amount.

14. The adjustable support as claimed in claim 11 wherein said bolt member is formed with a recess for a driving member and said stem portion has a hexagonal periphery.

15. A method of angularly adjusting an abutment member for a prosthetic tooth, comprising:
(a) a hollow prosthesis receiving abutment member having two open ends, an exterior surface and an interior surface with said interior surface receiving and retaining a head portion of a bolt member and permitting a stem portion of the bolt member to extend from one of said opening,
(b) forming said head portion shape so as to be complementary with respect to said interior surface,
(c) rounding an exterior portion of the abutment member where the stem portion extends from one of said openings,
(d) forming a nut member with a concave section to engage the rounded portion of the abutment member to permit positioning of the abutment member at different predetermined pivot positions with respect to the nut member, and (e) locking the abutment member in one of the predetermined pivoted positions by engaging the nut member with the step portion of the bolt member a predetermined amount to sandwich the abutment member between the head portion and the concave section.

16. The method as claimed in claim 15 including threading the inside of the abutment member to receive supporting structure for a bridge.

* * * * *